United States Patent [19]

Schroeder

[11] Patent Number: 5,259,377
[45] Date of Patent: Nov. 9, 1993

[54] ENDOTRACHEAL TUBE STYLET

[75] Inventor: Michael G. Schroeder, Rockford, Mich.

[73] Assignee: Stephen M. Daugherty, Walker, Mich.

[21] Appl. No.: 859,825

[22] Filed: Mar. 30, 1992

[51] Int. Cl.⁵ .............................................. A61M 37/00
[52] U.S. Cl. ........................... 128/207.14; 128/200.24; 604/95; 606/108
[58] Field of Search .................. 606/108; 604/95, 170, 604/282; 128/207.14, 207.18, 200.26, 200.24

[56] References Cited

U.S. PATENT DOCUMENTS

| | | | |
|---|---|---|---|
| 2,865,374 | 12/1958 | Brown et al. | 128/207.29 |
| 3,754,554 | 8/1973 | Felbarg | 128/200.26 |
| 3,776,222 | 12/1973 | Smiddy | 128/6 |
| 3,802,440 | 4/1974 | Salem et al. | 128/200.26 |
| 3,854,473 | 12/1974 | Matsuo | 128/8 |
| 3,996,939 | 12/1976 | Sheridan et al. | 128/207.14 |
| 4,244,362 | 1/1981 | Anderson | 128/200.26 |
| 4,245,624 | 1/1981 | Komiya | 128/4 |
| 4,329,983 | 5/1982 | Fletcher | 128/207.14 |
| 4,498,473 | 2/1985 | Gereg | 128/207.15 |
| 4,516,972 | 5/1985 | Samson | 604/282 |
| 4,529,400 | 7/1985 | Scholten | 604/95 |
| 4,756,708 | 7/1988 | Martin | 604/93 |
| 4,793,327 | 12/1988 | Frankel | 128/12 |
| 4,819,619 | 4/1989 | Augustine et al. | 128/200.26 |
| 4,825,858 | 5/1989 | Frankel | 128/200.26 |
| 4,827,925 | 5/1989 | Vilasi | 128/207.14 |
| 4,898,577 | 2/1990 | Badger et al. | 604/53 |
| 4,909,787 | 3/1990 | Danforth | 604/95 |
| 4,949,716 | 8/1990 | Chenoweth | 128/207.14 |
| 4,960,122 | 10/1990 | Mizus | 128/207.14 |
| 4,976,688 | 12/1990 | Rosenblum | 604/95 |
| 5,042,475 | 8/1991 | LaBombard | 128/207.14 |
| 5,058,577 | 10/1991 | Six | 128/200.26 |

FOREIGN PATENT DOCUMENTS

| | | | |
|---|---|---|---|
| 990417 | 9/1951 | France | 604/95 |
| 9111213 | 3/1973 | World Int. Prop. O. | 604/95 |

Primary Examiner—Edgar S. Burr
Assistant Examiner—Eric P. Raciti
Attorney, Agent, or Firm—Varnum, Riddering, Schmidt & Howlett

[57] ABSTRACT

A stylet for use in both oral and nasal endotracheal intubation comprises a flexible member, a collar slidably mounted thereon, a handle mounted at one end of and along the longitudinal axis of the flexible member and a fixed length filament attached to a distal end of the flexible member and the collar. A portion of the stylet is telescopically received within an endotracheal tube. The user may selectively deflect or induce curvature to the endotracheal tube by applying force to the handle along the axis of the flexible member and inducing movement of the handle with respect to the collar when the filament is under tension. Alternatively, the user may selectively deflect the endotracheal tube by inducing movement of the collar with respect to the handle when the filament is under tension.

24 Claims, 7 Drawing Sheets

ENDOTRACHEAL TUBE STYLET

BACKGROUND OF THE INVENTION

1. Field of the Invention

This invention relates to oral and nasal intubation devices and more particularly to a stylet and method of use for both oral and nasal intubation with an endotracheal tube.

2. Description of Related Art

Endotracheal tubes are utilized in a wide variety of medical procedures to provide an unobstructed air passage to a patient's trachea. In many emergency situations it is necessary to intubate a patient as quickly as possible to provide a secure airway to the patient's lungs or permit forced ventilation thereof while preventing introduction of gastric contents. Failure to quickly supply oxygen to the lungs can result in brain damage or death of the patient.

Endotracheal tubes are used orally and nasally to establish an open airway. Intubation is often difficult because of the contours and obstacles encountered in the patient's airway. Perhaps the most difficult step in intubating a patient is maneuvering the tube into the patient's trachea rather than the patient's esophagus.

Endotracheal tubes are generally formed of a soft, pliable plastic materials. Most endotracheal tubes do not have sufficient strength or rigidity to permit intubation without the aid of a stylet or other manipulating device. Making the endotracheal tube out of a stiffer material is not an acceptable alternative because it would cause excessive trauma to the nasal or throat tissue. The accepted solution has been the use of a stylet telescopically received within the endotracheal tube.

The stylet which has gained the most acceptance for oral intubation is a "pre-bend" stylet made of a rigid, malleable material such as rubber-coated metal. To intubate a patient with any stylet, the patient must first be hyperventilated for approximately three to four minutes. Next, the user inserts the stylet into the tube and folds one end of the stylet around the outboard end of the endotracheal tube. The user grasps the tube and the stylet and bends the tube to approximate what the user believes the contour of the patient's throat to be. With the help of a laryngoscope, the user inserts the stylet and endotracheal tube into the patient's mouth and throat until it reaches the patient's trachea. Unfortunately, without years of experience, it is difficult for a user to obtain the proper pre-bend in the malleable stylet and successfully insert the endotracheal tube into the patient's trachea. To complicate this further, each patient's airway is different.

If the user fails to intubate the patient on the first attempt, she must remove the tube and stylet from the patient, grasp the tube and stylet, rebend it accordingly, re-ventilate the patient and again insert the tube and stylet into the patient.

One problem with the malleable stylet is the valuable time lost as the user ventilates the patient and reinserts the tube and stylet repeatedly. Secondly, repeated insertions of the tube and stylet damages the patient's soft airway tissue. Finally, the malleable stylet sacrifices sterility of the endotracheal tube when the user grasps the tube and stylet to bend and rebend the stylet.

Mechanical guides have been developed to assist intubation of endotracheal tubes. However, none of these stylets have met with widespread commercial success or recognition in the medical field. The malleable or "prebend" stylet is still the predominate oral intubation aid used.

One example of a mechanical intubation guide is seen in U.S. Pat. No. 4,329,983 issued May 18, 1982, to Fletcher. The guide of Fletcher comprises a flexible bar and flexible line wherein the line extends both through and along the bar. One end of the line is attached to one end of the bar and the other end of the line is attached to a pivotable toggle offset from the axis of the flexible bar. Because the user is typically holding the laryngoscope in one hand for oral intubation, she only has one hand free to manipulate the intubation guide. The pivotable toggle mechanism of Fletcher is difficult if not impossible to manipulate with one hand. In addition, the pivotable toggle of Fletcher makes it difficult to control the end of the flexible bar and feel the flexible bar and tube during intubation. The ability to feel and control the movement of the stylet and endotracheal tube is vital for quick intubation and to avoid damaging the sensitive tissues encountered during intubation.

Another example of a mechanical intubation mechanism with an offset actuator is disclosed in U.S. Pat. No. 4,529,400 issued Jul. 16, 1985, to Scholten. This mechanism utilizes a chain-link stylet which is manipulated by a pivotable handle offset from the axis of the stylet. Once again, the pivotable handle of this mechanism suffers from a lack of delicate control and sensitivity helpful in successfully intubating a patient quickly with a minimum amount of trauma to sensitive tissue.

Another example of a mechanical intubation device is disclosed in U.S. Pat. No. 4,949,716 issued Aug. 21, 1990, to Chenoweth. This mechanical device is utilized for nasal intubation and utilizes a cooperable spring and wire mounted within a plastic sheath. As with the other stylet devices, the handle for manipulating the stylet is offset from the axis of the stylet thereby eliminating the control and sensitivity necessary to successfully intubate the patient.

SUMMARY OF INVENTION

The intubation device according the invention overcomes the problems of the prior art by creating a simple, easy to use endotracheal stylet which gives the user greater control over the movement of the stylet and the ability to feel and sense the movement of the stylet within the patient. In addition, use of the stylet according to the invention does not require the user to grasp the sterile endotracheal tube and thereby sacrifice the sterility of the tube. More importantly, a single stylet according to the invention can be utilized for both oral and nasal intubation.

A stylet for endotracheal intubation comprises an elongated flexible member adapted to fit within the length of an endotracheal tube. The flexible member, has a proximal end and a distal end. A handle is mounted on the longitudinal axis of the flexible member on the proximal end thereof. A fixed length filament has a second end attached to the distal end of the flexible member and a first end adjacent the handle. A collar is fixed to the first of the fixed length filament. The filament has an effective length sufficiently less than the length of the flexible member so that the flexible member is deformed to a curved condition in response to squeezing the handle and the collar together.

In a further embodiment, the elongated flexible member is tapered such that the cross sectional area of the proximal end is greater than the cross section area of the distal end.

In yet another embodiment, the filament is chosen from the group of flexible plastics, wire, coated metal wire and textile string.

In another embodiment, the flexible member, handle, collar and fixed-length filament are integrally molded as a single unit.

In a further embodiment, the collar has a slot formed thereon for mounting the collar on the flexible member.

In yet another embodiment, the first end of the filament is integrally molded into the collar.

In yet another embodiment, the second end of the filament is integrally molded into the distal end of the flexible member.

In one embodiment, the first end of the filament is received in a second aperture of the collar. Preferably, the collar is rectangular in shape.

In yet another embodiment, the second end of the filament is received in an aperture at the distal end of the flexible member.

In a further embodiment, a stop is mounted to the flexible member to limit the length of the flexible member which can be inserted into an endotracheal tube.

In yet another embodiment, a groove is formed in said stop being adapted to permit sliding movement of the filament through said groove.

An endotracheal tube assembly according to the invention comprises an endotracheal tube formed from a soft pliable material having a distal end and a proximal end. A stylet according to the invention is mounted in the endotracheal tube with the distal end of the flexible member adjacent the distal end of the endotracheal tube. The collar is mounted adjacent the proximal end of the tube for movement between the proximal end of the tube and the handle. Alternatively, the handle is mounted a spaced distance from the proximal end of the tube for movement between said spaced distance of the proximal end of the tube and the collar.

A method for mounting an endotracheal tube in a patient's tracheal opening comprises the steps of providing an endotracheal tube assembly as described above. Next, the user grasps the handle and collar of the stylet with one hand and inserts the distal end of the endotracheal tube and stylet into one of the patient's mouth or nose. The endotracheal tube is selectively deformed to induce curvature of the tube and stylet by squeezing the handle and the collar together to conform the shape of the endotracheal tube to the patient's airway. The distal end of the endotracheal tube is inserted into the patient's tracheal opening and finally the stylet is removed from the endotracheal tube.

A further step for the method according to the invention comprises the step of first removing the stylet and endotracheal tube from sterile packaging before grasping the handle and collar of the stylet.

A further step for mounting an endotracheal tube in a patient's tracheal opening comprises the step of mounting a supply of pressurized gas to the proximal end of the endotracheal tube.

BRIEF DESCRIPTION OF THE DRAWINGS

The invention will now be described with reference to the drawings wherein.

DESCRIPTION OF THE PREFERRED EMBODIMENT

Figure 1:
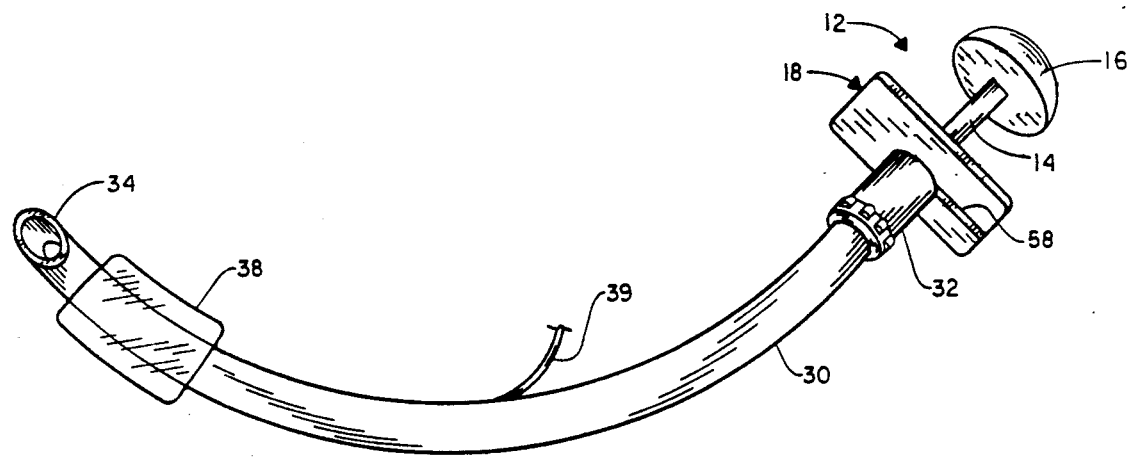
FIG. 1 is a perspective view of the first embodiment of the stylet according to the invention.
Figure 2:
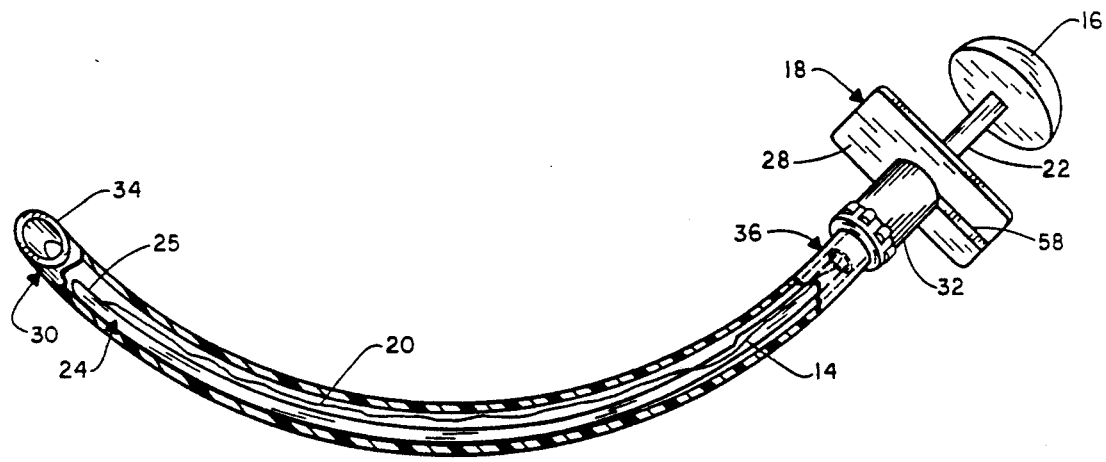
FIG. 2 is a partial sectional view of the first embodiment of the stylet mounted in an endotracheal tube in the relaxed state.

Referring now to the drawings and to FIGS. 1 and 2 in particular, a first embodiment of a stylet 12 comprises an elongated flexible member 14, a handle 16, a collar 18, and a fixed-length filament 20. The flexible member 14 has a proximal end 22 and a distal end 24. The effective length of the filament 20 is less than the length of the flexible member 14. A first end of the filament 20 is attached to the collar 18. The first end of the filament is attached to a flange 28 of the collar 18 which is offset from the longitudinal axis of the flexible member 14. The second end of the filament 20 is attached to an upper surface 25 at the distal end 24 of the flexible member 14. The flange 28 of the collar 18 is adjacent the upper surface 25 of the flexible member 14. The collar 18 has an aperture 26 (FIG. 4) dimensioned such that the collar can be slidably received on the flexible member 14.

The handle 16 is mounted to the proximal end 22 of the flexible member along the longitudinal axis of the flexible member 14.

As seen in FIG. 2, a portion of the stylet 12 is telescopically received within an endotracheal tube 30. The tube 30 has a proximal or outboard end 36 which remains outside of the intubated patient and a distal tapered end 34 which is inserted into the patient's oral or nasal cavity. The portion of the stylet 12 received within the tube 30 is the body portion between the distal end 24 of the flexible member 14 and the collar 18. The dimensions of the collar 18 are larger than the opening of the endotracheal tube so that the collar 18 cannot enter the endotracheal tube 30.

The endotracheal tube 30 has a fitting 32 mounted on the outboard end 36. The fitting 32 is suitable for attaching ventilation apparatus, an oxygen supply, anesthesia or other suitable gas (not shown). The fitting is conventional and of standard construction.

The tapered end 34 of the endotracheal tube 30 is contoured to permit insertion of the tube 30 into a patient. Use of a tapered end 34 causes less trauma to the patient's tissue than a blunt end and is therefore preferred. Endotracheal tubes which are suitable for use with the stylet according to the invention are conventional.

As seen in FIG. 1, endotracheal tubes typically incorporate an inflatable collar 38 adjacent the distal tapered end 34 and a conduit 39. The conduit 39 is in communication with the inflatable collar 38 and provides means to inflate and deflate the inflatable collar 38. During intubation, the inflatable collar 38 is deflated. Once the patient is successfully intubated, the inflatable collar 38 is inflated through the conduit 39 to prevent the ventilation gas flowing through the endotracheal tube 30 from escaping. The ventilation gas is directed into the patient's lungs. The inflatable collar 38 is deflated through the conduit 39 prior to removal of the endotracheal tube 30 from the patient.

The collar 18 of the first embodiment is slidably mounted on the flexible member 14 and, as noted above, the effective length of the filament 20 is less than the length of the flexible member 14. Therefore, as the collar 18 is pulled toward the handle 16, a point will be reached where the filament 20 is placed under tension. If the user continues to apply additional force to slide the collar 18 toward the handle 16, then the flexible member 14 will bend such that the upper surface 25 is on the inside radius of the curve. An alternative to moving the collar 18 with respect to the handle 16 is to hold the collar 18 fixed and slide the proximal end of the flexible member 14 and handle 16 toward the collar. Regardless of which element is moved, the stylet 12 is bent. The bending of the stylet 12 while mounted within the endotracheal tube 30 also bends the tube 30 and permits manipulation of the endotracheal tube 30 during intubation of a patient.

In the first embodiment, the cross sectional area of the flexible member 14 is greater at the proximal end 22 than at the distal end 24. Therefore, as the flexible member 14 is bent by the movement of the collar 18 with respect to the handle 16 and flexible member 14, the distal end 24 of the flexible member 14 will deform more easily than the proximal end 22. Therefore, the curvature of the flexible member 14 will initiate at the distal end 24 rather than the body or proximal end 22 thereof. It is anticipated that the flexible member 14 could have a uniform cross sectional area to create uniform curvature of the flexible member upon deflection, or one specific area, such as the distal end 24 of the flexible member could have a reduced cross sectional area for enhanced curvature.

The endotracheal tube is typically pre-bent as seen in FIGS. 1 and 2. In FIG. 2 the stylet 12 is seen telescopically mounted in an endotracheal tube in the relaxed state. The fixed-length filament 20 is not tensioned, however the flexible member 14 is bent to conform to the curvature of the tube 30. The collar 18 abuts the fitting 32 of the outboard end 36 of the tube 30.

Figure 3:
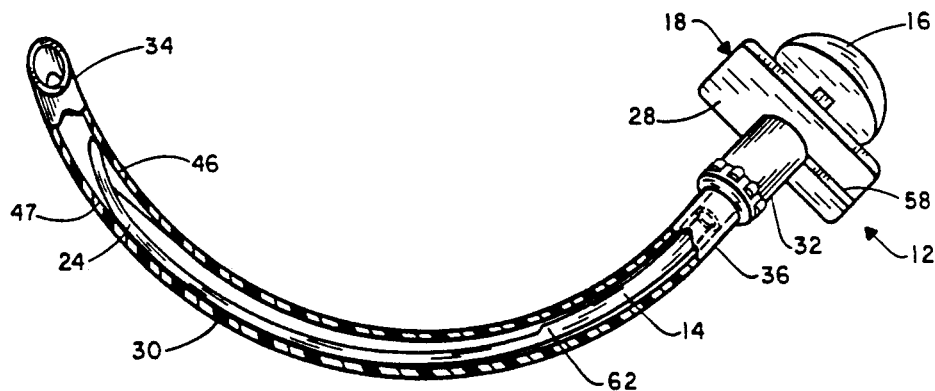
FIG. 3 is a partial sectional view of the first embodiment of the stylet mounted in an endotracheal tube in the tensioned state.

FIG. 3 shows the stylet telescopically mounted in the endotracheal tube in the tensioned state. A squeezing force has been applied to the handle 16 along the axis of the flexible member 14 while the collar 18 has been held fixed by abutting engagement with the fitting 32. As a result of the force applied to the handle 16, the filament 20 is under tension and the flexible member 14 has been deformed to create a desired amount of curvature. As seen in FIG. 3, the distal end of the flexible member has been flexed such that it contacts the upper surface 46 of the endotracheal tube 30. However, the body portion of the flexible member 14, spaced a short distance away from the distal end 24, abuts the lower surface 47 of the endotracheal tube 30. The contact of the distal end 24 of the flexible member with the upper surface 46 and the body portion of the flexible member 14 abutting the lower surface 47 of the tube 30 creates enhanced curvature at the tapered end 34 of the endotracheal tube 30. The curvature may be selectively increased or decreased as the user guides the tube 30 and stylet 12 during intubation by increasing or decreasing the squeezing force applied to the handle 16.

Figure 4:
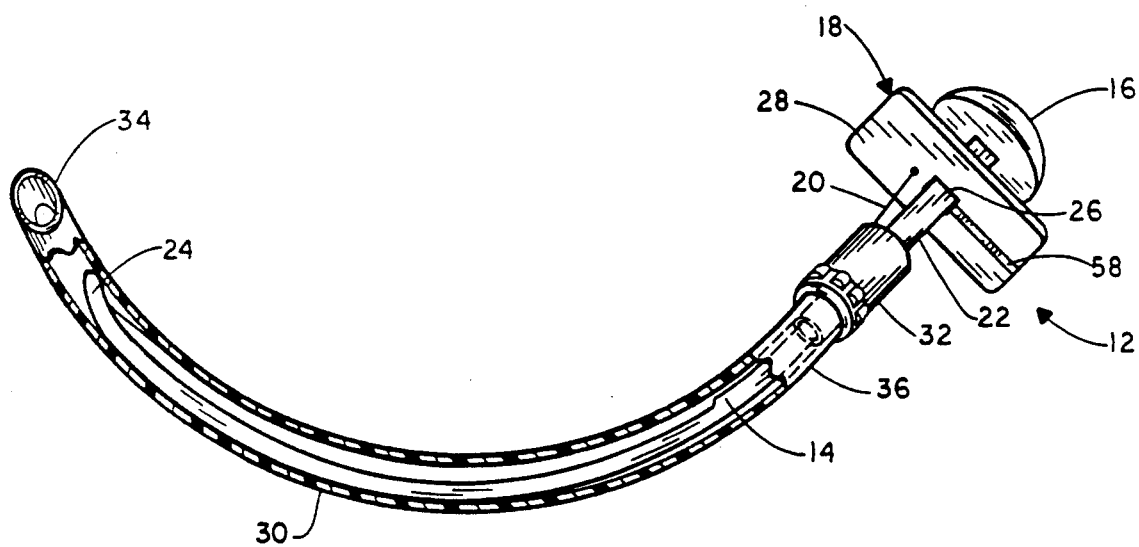
FIG. 4 is a partial sectional view of the first embodiment of the stylet mounted in an endotracheal tube in an alternative tensioned state.

As discussed above, the same curvature can be accomplished by sliding the collar toward the handle. FIG. 4 shows the stylet in the tensioned state where a squeezing force has been applied to the collar, pulling the collar toward the handle 16 along the axis of the flexible member 14 while the handle 16 has not moved with respect to the endotracheal tube 30. This alternative method creates the same curvature of the flexible member 14 and endotracheal tube 30.

Figure 5:
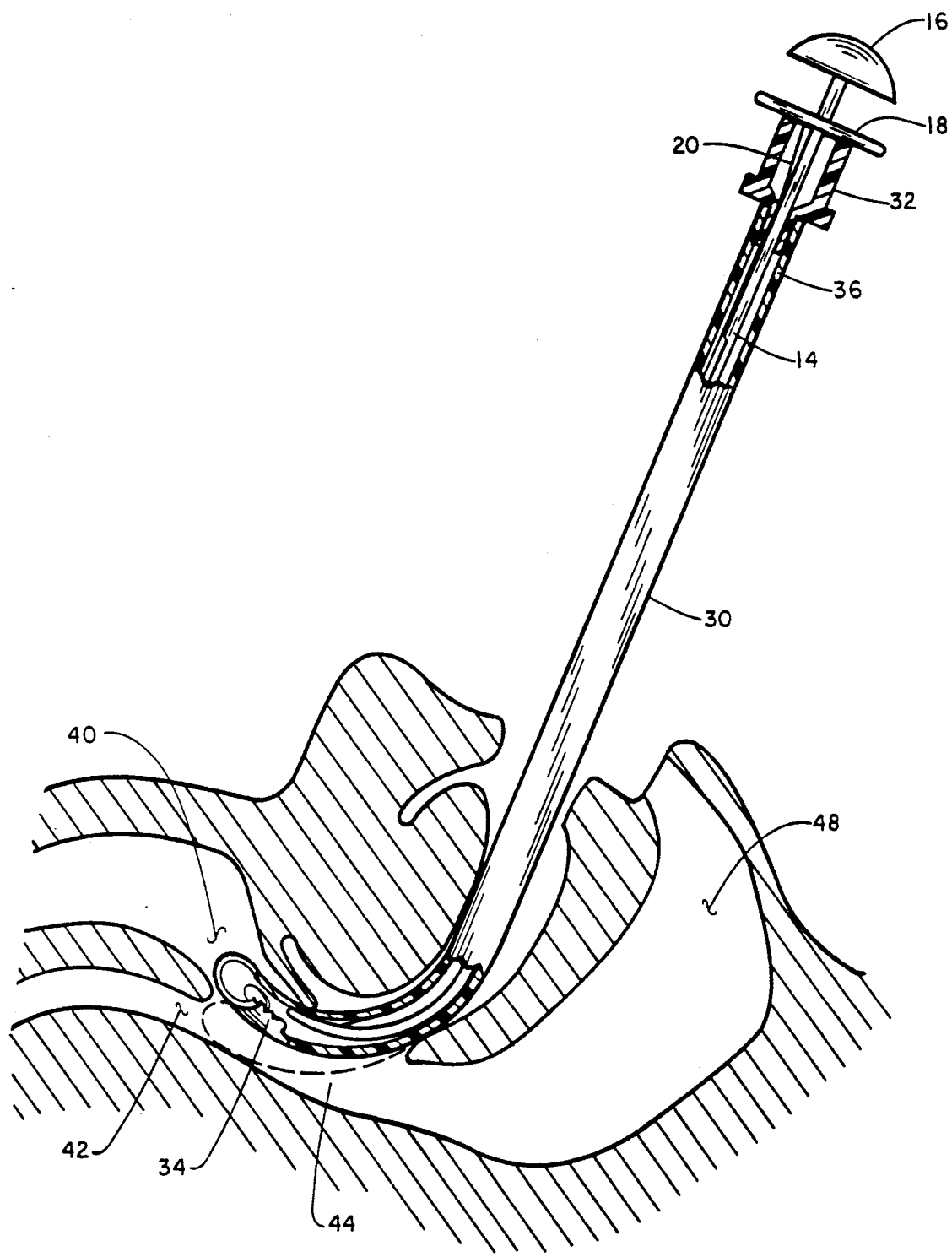
FIG. 5 is a partial sectional view of oral intubation of a patient utilizing the stylet according to the invention.

The intubation stylet, according to the invention, is suitable for use in both oral and nasal intubation. FIG. 5 shows oral intubation with the stylet according to the invention. In operation, the stylet 12 and endotracheal tube 30 are first removed from their sterilized packages (not shown). Next, the body portion of the stylet 12 is telescopically received in the outboard end 36 of the endotracheal tube 30. The length of the stylet is such that the distal end of the stylet 24 is adjacent the tapered end 34 of the tube 30, but does not extend beyond the tapered end 34. The patient's head is tilted back to open the airway. The tapered end 34 of the endotracheal tube 30 and flexible member 14 are then inserted into the patient's mouth and guided down the patient's throat until reaching the tracheal opening 40. If the endotracheal tube 30 and stylet 12 were merely inserted further into the airway, the tapered end 34 of the endotracheal tube 30 would remain in the patient's esophagus 42.

To successfully insert the endotracheal tube 30 into the patient's tracheal opening 40, the user must deflect the tapered end 34 of the endotracheal tube 30 toward the tracheal opening 40. To create this deflection with the stylet 12 according to the invention, the user applies a squeezing force to the handle 16 and the collar 18 to achieve enhanced curvature of the distal end 24 of the flexible member 14. Then, the user can insert the endotracheal tube further into the patient's airway to cause the tapered end 34 to enter the tracheal opening 40. Finally, the user removes the stylet 12 from the tube 30 and attaches ventilation apparatus, if necessary, to the fitting 32.

The stylet 12 according to the invention selectively alters the curvature of the flexible member 14 and more specifically the distal end 24 as the tube is being inserted into the patient's mouth and throat. Selectively curving the tube 30 during all stages of inserting the tube 30 into the patient can be helpful. Curving the endotracheal tube 30 and the flexible member 14 during the initial stages of intubation is helpful to quickly and easily insert the endotracheal tube into the patient's mouth and throat and avoid trauma to the sensitive throat tissues. As discussed above, deflecting the tube 30 toward the endotracheal opening in the later stages of intubation is vital in successfully intubating a patient.

During intubation, the patient is usually lying horizontally with his head tilted back. The user of the endotracheal tube would typically stand adjacent to the top of the patient's head. With one hand, the user would insert a laryngoscope (not shown) into the patient's mouth. With the other hand, the user would grasp and manipulate the stylet 12 and endotracheal tube 30 while looking into the laryngoscope. The stylet 12 according to the invention gives the user greater sensitivity and control over the endotracheal tube during intubation.

In use, the user would typically wrap her fingers around the outboard end 36 of the endotracheal tube 30 such that her forefinger surrounds the fitting 32 of the tube 30. The user would place her thumb on the handle 16 of the stylet 12 and move the handle 16 and flexible member 14 with respect to the collar 18 by selectively applying force to the handle 16. Movement of the collar 18 is prevented by the user's fore-finger or the outboard end 36 of the endotracheal tube. Therefore, the stylet 12 is inserted further into the tube 30 while the filament is prevented from insertion because of the collar 18. This causes the deflection of the flexible member 14 and tube 30.

By grasping the outboard end 36 of the endotracheal tube 30 with her fingers and by applying the force to deflect the flexible member 14 with her thumb to the handle 16 along the axis of the flexible member 14, the user can directly sense resistance to this movement. In addition, by applying the force directly along the axis of the flexible member 14, the user can more directly control the amount of deflection induced in the flexible member 14. The enhanced sensitivity and greater control over the stylet during intubation increases the chance of successfully intubating the patient on the first attempt.

Other benefits of the stylet according to the invention lie in the fact that there is no need to remove the endotracheal tube 30 and stylet 12 from the patient if the user does not successfully intubate the patient on the first try. The user can apply more or less force to the flexible member to vary the deflection of the distal end 24 as the user manipulates the tapered end 34 of the endotracheal tube 30 into the tracheal opening 40.

Figure 6:
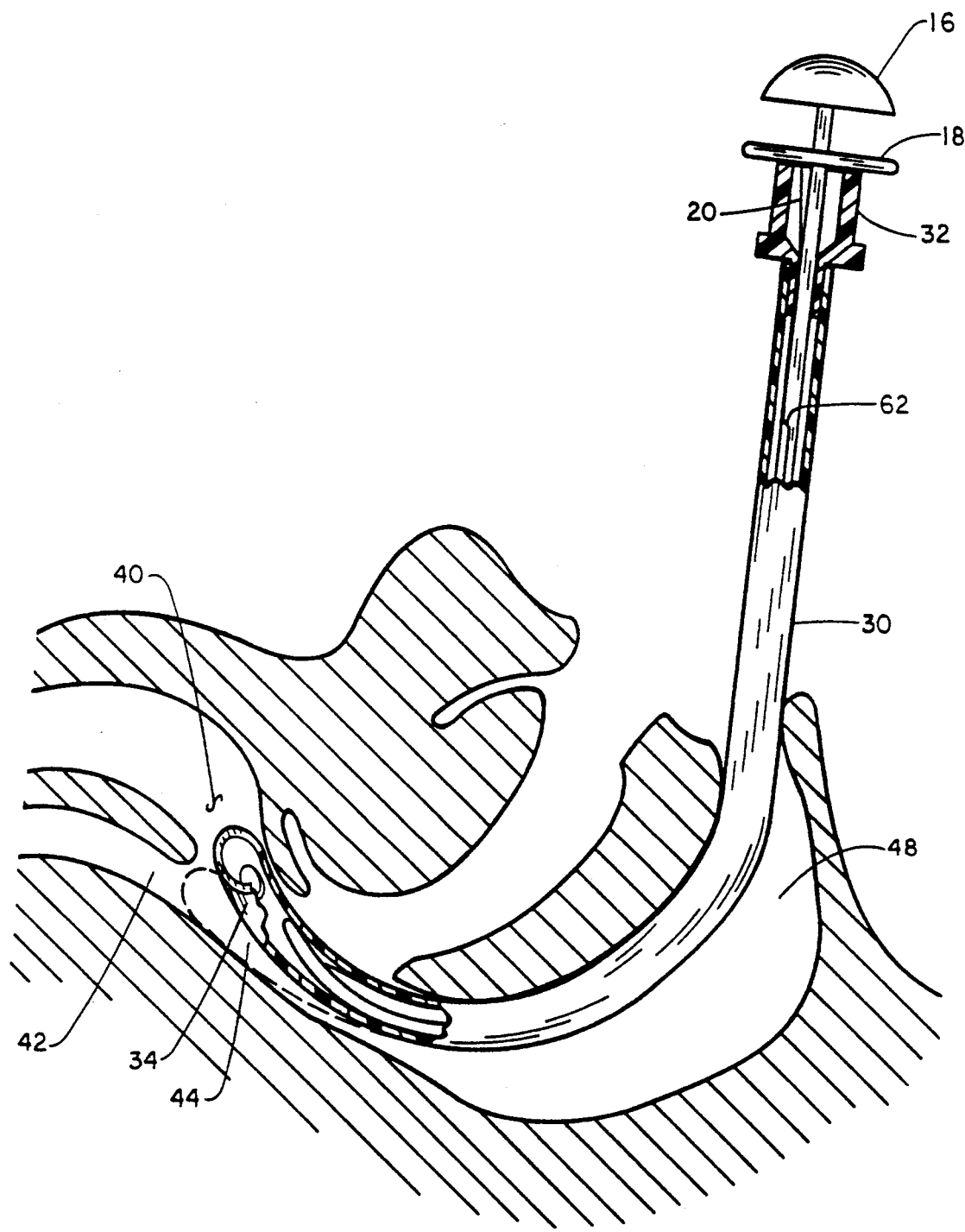
FIG. 6 is a partial sectional view of nasal intubation of a patient utilizing the stylet according to the invention.

The process of nasal intubation of a patient utilizing the stylet according to the invention is seen in FIG. 6. Nasal intubation presents the same problem of deflecting the tapered end 34 of the endotracheal tube 30 away from the esophagus 42 and into the tracheal opening 40 at the latter stages of intubation. The stylet 12, according to the invention, is utilized, as earlier described. The flexible member 14 is curved by applying force to the handle 16 to move the handle 16 with respect to the collar 18, or applying force to the collar 18 to move the collar 18 with respect to the handle, thereby tensioning the filament 20. As more force is applied, the flexible member 14 is curved or deflected. The curvature of the flexible member 14 deflects the endotracheal tube 30 to accommodate insertion of the endotracheal tube into the patient's nasal cavity 48, throat 44 and ultimately into the patient's tracheal opening 40.

In the first embodiment as seen in FIGS. 1-6, the first end of the fixed-length filament is integrally molded to the upper surface 25 of the distal end 24 of the flexible member 14. Similarly, the second end of the filament 20 is integrally molded into the collar 18. This creates a unitary stylet. A slot 58 is incorporated into the collar 18 to slidably mount the collar 18 on the flexible member 14. The opening of the slot 58 is dimensioned such that the collar 18 can be selectively mounted to the narrower distal end 24 of the flexible member 14 but cannot be removed from the thicker proximal end 22. By integrally molding the flexible member, the filament and the collar 18, there are no separable parts which can be lost from the overall structure.

Figure 7:
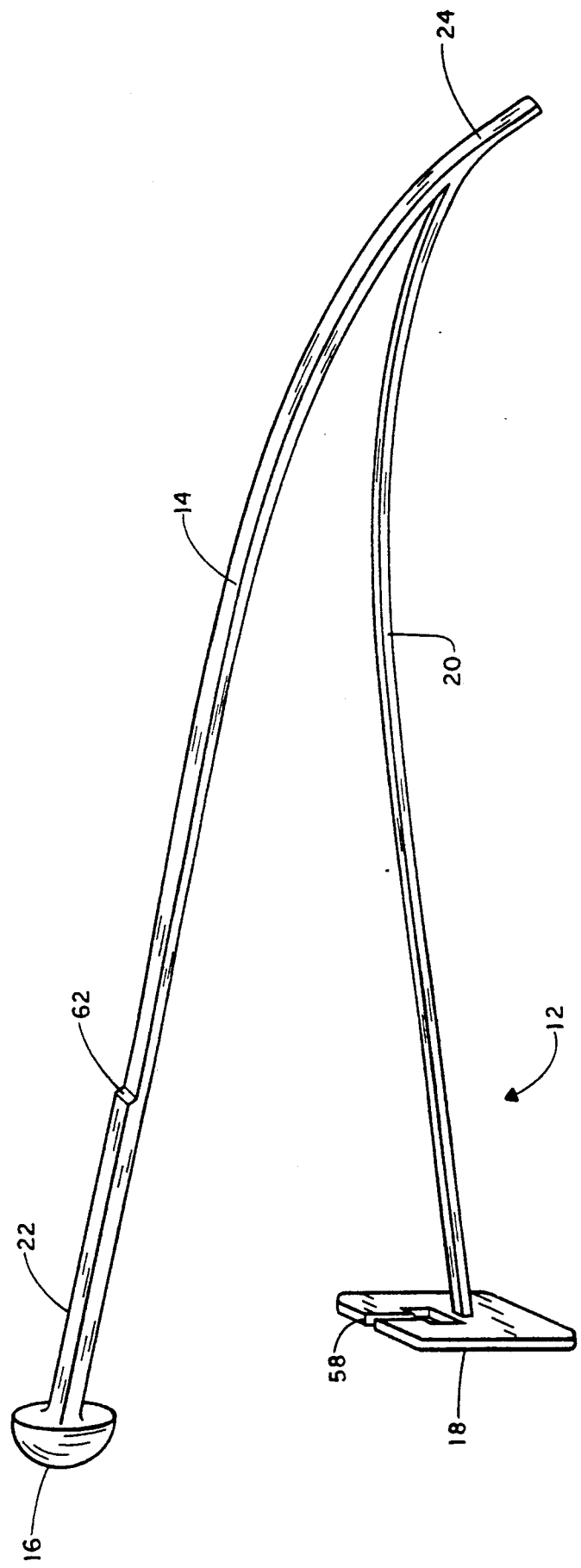
FIG. 7 is a perspective view of the preferred embodiment of the stylet according to the invention.

The preferred embodiment of the stylet is seen in FIG. 7. In this embodiment, the stylet 12 is molded as a single, unitary article. The stylet 12 can be made from any material which is deformable and yet has sufficient strength for intubation. Examples of a suitable material include nylon, high density polyethylene, and polystyrene.

Similar to the first embodiment (FIGS. 1-6), the preferred embodiment of the stylet 12 comprises a flexible member 14, a handle 16 and a fixed-length filament 20. The handle 16 is molded on the proximal end 22 of the flexible member 14 along the longitudinal axis thereof. A collar 18 is molded on the second end of the filament 20. The collar 18 incorporates a slot 58 to permit the collar to be mounted on the proximal end 22 of the flexible member 14. The distal end 24 of the flexible member 14 is molded to the first end of the fixed-length filament 20.

The preferred embodiment of the stylet 12 as seen in FIG. 7 operates in the same manner as previously described for the first embodiment. A squeezing force applied to the handle 16 with respect to the collar 18 causes deflection of the flexible member 14. Alternatively, the handle 16 can be held in place and the collar 18 can be pulled toward the handle 16 to cause deflection of the flexible member 14. It is important to note that the slot 58 of the collar 18 is not a necessary element of the stylet 12. The slot 58 merely guides the collar 18 as the collar 18 moves with respect to the handle 16 or vice versa.

Figure 8:
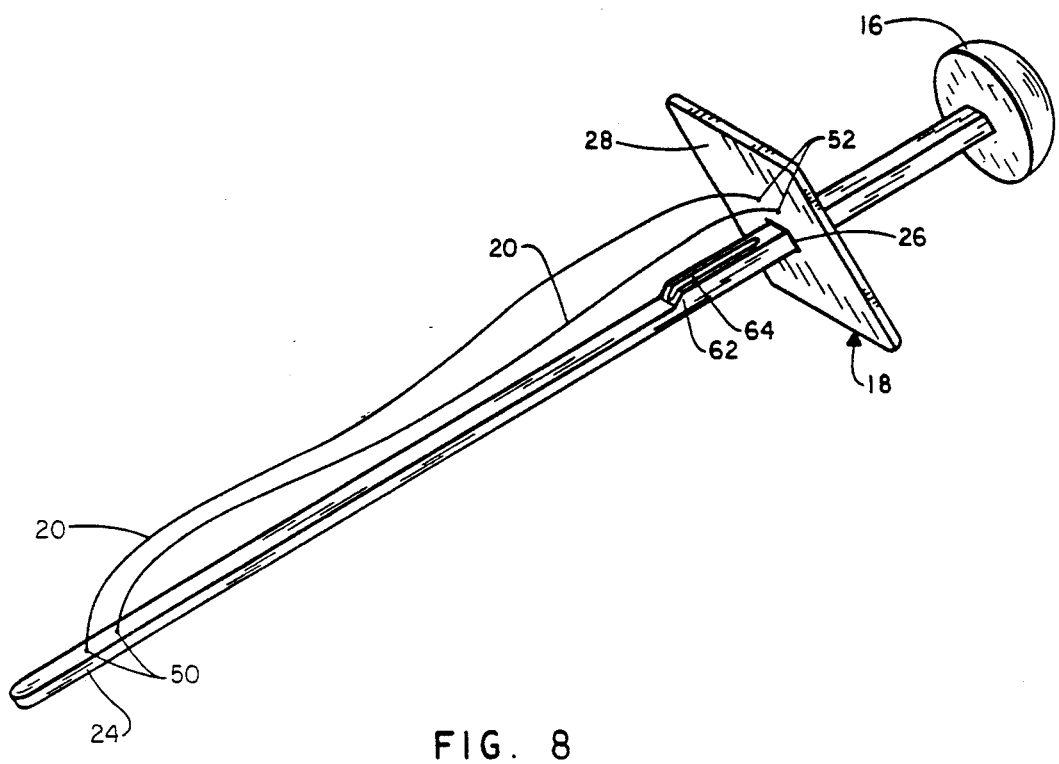
FIG. 8 is a perspective view of an alternative embodiment of the stylet according to the invention.

A third embodiment of the stylet according to the invention is seen in FIG. 8. In this embodiment, the fixed-length filament 20 is mounted to the collar 18 and flexible member 14 by mechanical means. The collar 18 is first slidably mounted on the flexible member 14. Next, the fixed-length filament 20 is looped through openings 50 at the distal end 24 of the flexible member such that only a short length of the filament lies along the lower surface of the flexible member 14. The ends of the fixed-length filament 20 pass through openings 52 in the flange 28 of the collar 18 and are tied off, creating a loop. The openings 52 in the flange 28 are offset from the aperture 26 which is mounted along the longitudinal axis of the flexible member The mechanical means for attaching the filament 20 to the collar 18 and flexible member 14 of the third embodiment create a unitary stylet 12 and function in the same manner as described above for the first embodiment. An alternative to creating a loop of the fixed length filament 20 would be to tie a knot in the end of the filament after it passing it through the opening 52 in the flange and the opening 50 of the flexible member provided the knots are larger than the diameter of the openings 50 and 52.

The diameter and length of endotracheal tubes vary for different applications. The stylet 12 and endotracheal tube 30 shown in FIGS. 1-8 are suitable for use with adults. However, smaller patients, such as children, require a shorter length tube having a smaller diameter. The stylet 12 according to the invention is constructed such that a single size stylet 12 can be used in a wide range of sizes of endotracheal tubes.

As seen in FIG. 8, the stylet has a stop 62 formed on the flexible member spaced a distance from the handle 16. A groove 64 is also formed in the flexible member 14 and stop 62. The groove 64 is dimensioned such that the filament 20 can be slidably mounted therein. The stop 62 and groove 64 can be incorporated in all of the embodiments of the stylet 12 according to the invention.

Figure 9:
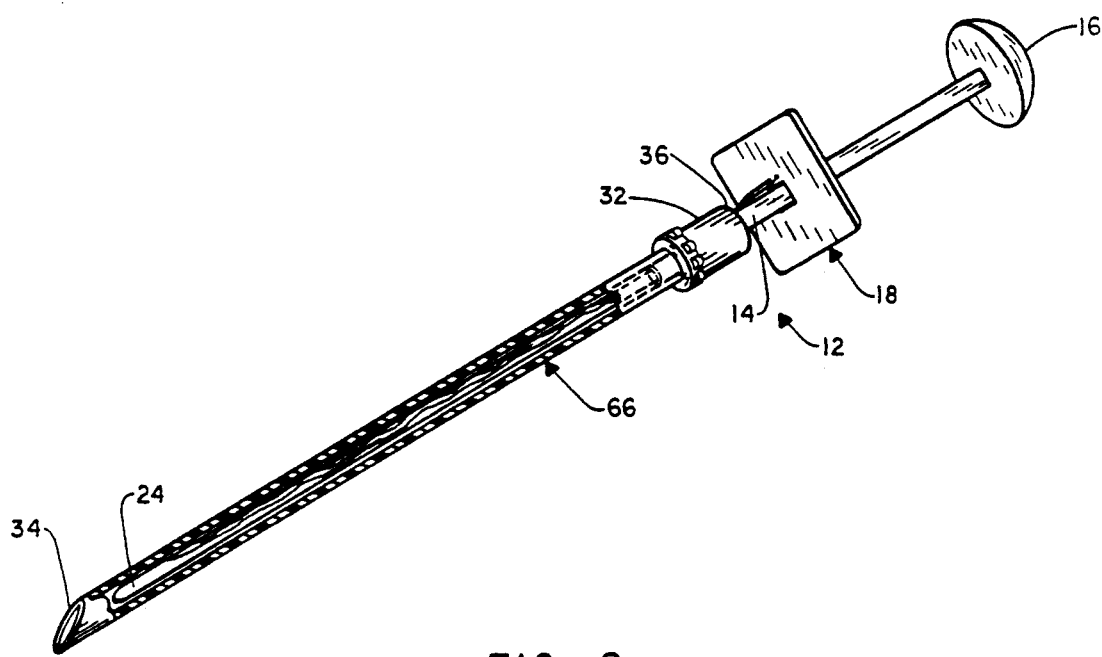
FIG. 9 is a partial sectional view of an alternative embodiment of the stylet mounted in an alternative endotracheal tube in the relaxed state.
Figure 10:
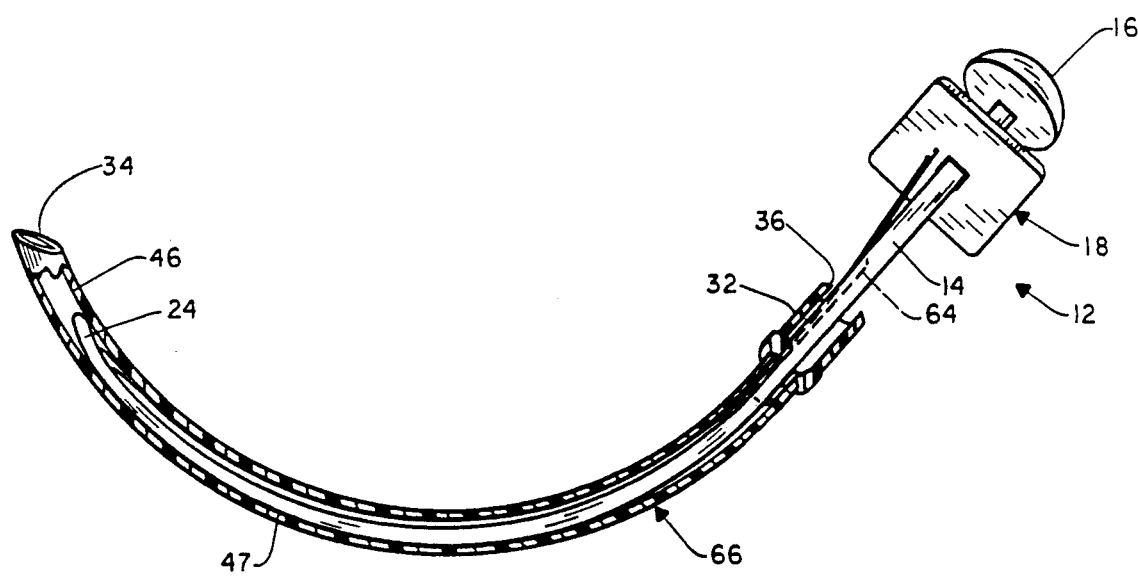
FIG. 10 is a partial sectional view of an alternative embodiment of the stylet mounted in an alternative endotracheal tube in the tensioned state.

As seen in FIGS. 9 and 10, an endotracheal tube 66 is seen having a shorter length and smaller diameter than the endotracheal tube 30 described above in FIGS. 1-6. The overall length of the stylet 12 exceeds the length of the endotracheal tube 66 therefore it is necessary to limit the length of the stylet which can be inserted into the tube 66. The body portion of the flexible member 14 between the stop 62 and the distal end 24 is dimensioned such that it can be telescopically received within the endotracheal tube 66. As seen in FIG. 10, the stop 62 contacts the fitting 32 and prevents the flexible member 14 from further insertion into the endotracheal tube 66. The stop 62 is located on the flexible member 14 at a position such that the distal end 24 of the flexible member 14 is immediately adjacent the tapered end 34 of the endotracheal tube 66 when the stylet 12 is fully mounted within the tube 66.

When utilizing the stylet 12 according to the invention and a smaller diameter and shorter length endotracheal tube 66, the collar 18 does not abut the fitting 32 or outboard end 36 of the endotracheal tube 66. Therefore, to cause deflection of the endotracheal tube 66, the user squeezes the collar 18 toward the handle 16, as seen in FIG. 10. Similar to the first embodiment, squeezing the handle 16 and collar 18 causes the distal end 24 of the flexible member 14 to curve such that the distal end 24 contacts an upper surface of the endotracheal tube 66. The body portion of the flexible member 14 abuts a bottom surface 47 of the endotracheal tube 66. This creates enhanced curvature of the tapered end 34 of the endotracheal tube 66.

The stylet 12 according to the invention creates a simple, economical and effective means to intubate a patient. The stylet can be easily operated with a single hand, thereby freeing the user's other hand for other operations such as controlling a laryngoscope. The construction and method of using the stylet give the user greater control and increased sensitivity, thereby making it easier to quickly intubate a patient and restore the airway. In addition, the sterility of the endotracheal tube can be maintained because of the user's minimum amount of contact with the distal end of the tube and stylet.

While particular embodiments of the invention have been shown, it will be understood, of course, that the invention is not limited thereto since modifications may be made by those skilled in the art, particular in light of the foregoing teachings. Reasonable variation and modification are possible within the foregoing disclosure of the invention without departing from the scope of the invention.

I claim:

1. A stylet selectively received in an endotracheal tube for endotracheal intubation comprising;
    an elongated flexible member having a longitudinal axis, a proximal end and a distal end and adapted to fit within the length of an endotracheal tube;
    a handle mounted on the longitudinal axis of said flexible member on the proximal end thereof;
    a fixed length filament having a first end adjacent said handle and a second end attached to said distal end of said flexible member; and
    a collar fixed to the first end of the fixed length filament, said filament having an effective length sufficiently less than the length of said flexible member so that said flexible member is deformed to a curved condition in response to squeezing the handle and the collar together.

2. A stylet according to claim 1 wherein said elongated flexible member is tapered such that the cross sectional area of proximal end is greater than the cross sectional area of the distal end.

3. A stylet according to claim 1 wherein said collar has a slot formed thereon for mounting said collar on said flexible member.

4. A stylet according to claim 1 wherein the flexible member, handle, collar and fixed-length filament are integrally molded as a single unit.

5. A stylet according to claim 1 wherein said first end of said filament is integrally molded into said collar.

6. A stylet according to claim 1 wherein said second end of said filament is integrally molded into said distal end of the flexible member.

7. A stylet according to claim 1 wherein said first end of said filament is received in a second aperture of said collar.

8. A stylet according to claim 1 wherein said second end of said filament is received in an aperture of said distal end of the flexible member.

9. A stylet according to claim 1 wherein said collar is rectangular in shape.

10. A stylet according to claim 1 further comprising a stop mounted to the flexible member to limit the length of the flexible member which can be inserted into an endotracheal tube.

11. A stylet according to claim 10 further comprising a groove formed in said stop being adapted to permit sliding movement of the filament through said groove.

12. A stylet for endotracheal intubation comprising;
    an elongated flexible member having a proximal end and a distal end;
    a handle integrally molded to the proximal end of said flexible member;
    a fixed length filament having a distal end and a proximal end, said distal end of the filament being integrally molded to the distal end of said flexible member; and
    a collar integrally molded to said proximal end of said fixed length filament
    whereby said flexible member is deformed to a curved condition in response to squeezing the handle and collar.

13. A stylet according to claim 12 wherein said elongated flexible member is tapered such that the cross sectional area of proximal end is greater than the cross sectional area of the distal end.

14. A stylet according to claim 12 wherein said collar has a slot formed thereon for mounting said collar on said flexible member.

15. A stylet according to claim 12 further comprising a stop mounted to the flexible member to limit the length of the flexible member which can be inserted into an endotracheal tube.

16. A method for mounting an endotracheal tube in a patient's airway comprising the step of;
    providing an endotracheal tube comprising;
        (a) an endotracheal tube having a distal end and a proximal end; and
        (b) a stylet having a proximal end and a distal end, a handle mounted to the proximal end of the stylet, and a collar fixedly interconnected to the distal end of the stylet by a fixed length filament, the fixed length filament having an effective length less than the length of the flexible member;

mounting the stylet in the endotracheal tube such that the distal end of the stylet is adjacent the distal end of the endotracheal tube and the handle of the stylet being adjacent to the proximal end of the tube;

grasping the handle and collar of the stylet with one hand;

inserting the distal end of the endotracheal tube and stylet into one of the patient's mouth or nose;

squeezing the handle and the collar together along the longitudinal axis of the stylet to selectively deform the endotracheal tube and stylet and induce curvature of the tube and stylet and conform the shape of the endotracheal tube to the patient's airway;

inserting the endotracheal tube distal end into the patient's tracheal opening; and removing the stylet from the endotracheal tube.

17. A method according to claim 16 further comprising the step of first removing the stylet and endotracheal tube from sterile packaging.

18. A method according to claim 16 further comprising the step of mounting a ventilating apparatus to the proximal end of the endotracheal tube.

19. An endotracheal tube assembly comprising
an endotracheal tube having a distal end and a proximal end, said tube being made from a soft pliable material; and
a stylet selectively mounted in the endotracheal tube comprising;
an elongated flexible member having a longitudinal axis, a proximal end and a distal end and adapted to fit within the length of the endotracheal tube;
a handle mounted on the longitudinal axis of said flexible member to the proximal end thereof;
a fixed length filament having a first end attached to said distal end of said flexible member and a second end adjacent said handle; and
a collar mounted on the second end of the fixed length filament, said filament having an effective length sufficiently less than the length of said flexible member so that said flexible member is deformed to a curved condition in response to squeezing the handle and the collar together;
the stylet being mounted in the endotracheal tube with the distal end of the flexible member adjacent the distal end of the endotracheal tube.

20. An endotracheal tube assembly according to claim 19 wherein the collar is mounted adjacent the proximal end of the tube for movement between the proximal end of the tube and the handle.

21. An endotracheal tube assembly according to claim 19 wherein the handle is mounted a spaced distance from the proximal end of the tube for movement between the spaced distance from the proximal end of the tube and the collar.

22. An endotracheal tube assembly comprising;
an endotracheal tube having a distal end and a proximal end, said tube being made from a soft pliable material; and
a stylet selectively mounted in the endotracheal tube comprising;
an elongated flexible member having a proximal end and a distal end;
a handle integrally molded to the proximal end of said flexible member;
a fixed length filament having a distal end and a proximal end, said distal end of the filament being integrally molded to the distal end of said flexible member; and
a collar integrally molded to said proximal end of said fixed length filament, said flexible member being deformed to a curved condition in response to squeezing the handle and collar;
the distal end of the flexible member being mounted adjacent the distal end of the endotracheal tube.

23. An endotracheal tube assembly according to claim 22 wherein the collar is mounted adjacent the proximal end of the tube for movement between the proximal end of the tube and the handle.

24. An endotracheal tube assembly according to claim 22 wherein the handle is mounted a spaced distance from the proximal end of the tube for movement between the spaced distance from the proximal end of the tube and the collar.

* * * * *